United States Patent
Drogemoller et al.

(12) 
(10) Patent No.: US 6,214,866 B1
(45) Date of Patent: Apr. 10, 2001

(54) COMPOSITION COMPRISING MUPIROCIN AND CHLORHEXIDINE

(75) Inventors: Monica Lucie Drogemoller, Rondebosch; Stanley Leslie Linley, Newlands, both of (ZA)

(73) Assignee: SmithKline Beecham Pharmaceuticals (Pty) Limited, Cape Province (ZA)

( * ) Notice: Subject to any disclaimer, the term of this patent is extended or adjusted under 35 U.S.C. 154(b) by 0 days.

(21) Appl. No.: 09/230,756

(22) PCT Filed: Jul. 29, 1997

(86) PCT No.: PCT/EP97/04165

§ 371 Date: Mar. 16, 1999

§ 102(e) Date: Mar. 16, 1999

(87) PCT Pub. No.: WO98/05313

PCT Pub. Date: Feb. 12, 1998

(30) Foreign Application Priority Data

Aug. 1, 1996 (GB) .................................. 9616208

(51) Int. Cl.$^7$ .................................. A61K 31/155
(52) U.S. Cl. ..................... 514/451; 514/460; 514/969
(58) Field of Search ................... 514/451, 460, 514/969

(56) References Cited

U.S. PATENT DOCUMENTS

| | | | |
|---|---|---|---|
| 3,758,686 | 9/1973 | Sieger et al. | 424/241 |
| 4,122,158 | 10/1978 | Schmitt | 424/27 |
| 4,790,089 | 12/1988 | Hunter et al. | 424/404 |
| 4,847,068 | 7/1989 | Dole et al. | 424/47 |
| 4,879,287 | 11/1989 | Orr et al. | 514/171 |
| 5,985,291 | * 11/1999 | De Wet | 424/400 |

FOREIGN PATENT DOCUMENTS

| | | |
|---|---|---|
| 0095897 A2 | 12/1983 | (EP) . |
| 0128228 A1 | 12/1984 | (EP) . |
| 0167856 A2 | 1/1986 | (EP) . |
| 0251434 A2 | 1/1988 | (EP) . |

OTHER PUBLICATIONS

Lawrence, et al., "Preliminary Studies of the Use of Mupirocin in the Treatment of Burns", *Royal Society of Medicine*, pp. 165–172 (1994).

Watanakunakorn et al., "Mupirocin ointment with and without chlorhexidine baths in the eradication of *Staphylococcus* etc.", *American Journal of Infection Control*, 23(5), pp. 306–309 (1995).

Rode et al., "Bactericidal Efficacy of Mupirocin in Multi--Antibiotic Resistant *Staphylococcus* etc.", *J. Antimicrob. Chemother.*, 21(5), pp. 589–596 (1988).

Copending Ser. No. USSN 08/903,255, now USP 6,025,389.
Copending Ser. No. USSN 08/977,934, now USP 5,985,211.

* cited by examiner

*Primary Examiner*—Frederick Krass
(74) *Attorney, Agent, or Firm*—Elizabeth J. Hecht; William T. King; Charles M. Kinzig

(57) ABSTRACT

Pharmaceutical compositions comprising mupirocin and chlorhexidine are of use in treating topical bacterial infections, in particular infected burn injuries.

11 Claims, No Drawings

COMPOSITION COMPRISING MUPIROCIN AND CHLORHEXIDINE

This application is a 371 of PCT/EP97/04165, filed Jul. 29, 1997.

The present invention relates to a pharmaceutical composition comprising mupirocin and chlorhexidine.

Mupirocin, formerly known as pseudomonic acid, is a therapeutically useful compound which exhibits good antibacterial activity, mainly against Gram-positive bacteria, but also against some Gram-negative bacteria such as *Haemophilus influenzae* and *Moraxella catarrhalis*. It acts as selective reversible inhibitor of bacterial iso-leucyl t-RNA synthetase, thereby inhibiting bacterial protein synthesis (see Merck Index, 11th edn, 1989, 993 and references therein). The compound has an ester moiety which is susceptible to metabolism, effectively excluding the systemic use of the compound. It is however clinically effective as a topical agent.

Topical antibacterial compositions comprising mupirocin are marketed by SmithKline Beecham under the trade names Bactroban Ointment and Bactroban Nasal. The first product is an ointment comprising a water soluble polyethylene glycol base (see also EP 0 095 897-A, Beecham Group) whilst the second product comprises the calcium salt of mupirocin in a white soft paraffin based ointment containing a glycerin ester (see also EP 0 167 856-A, Beecham Group). More recently, topical creams comprising mupirocin or a salt thereof have been described (PCT/US94/12026, SmithKline Beecham). The formulation comprising the calcium salt of mupirocin in a white soft paraffin based ointment containing a glycerin ester is particularly useful when applied to the anterior nares for the prophylatic eradication of the nasal carriage of *Staph aureus*.

More recently, De Wet has disclosed the results of a clinical study demonstrating the efficacy of a combination of mupirocin and chlorhexidine in treating infected areas of skin, in particular infected burns injuries (paper presented to South African Burns Society Congress on Oct. 16, 1994, Sun City, South Africa). Separate compositions of a mupirocin ointment (Bactroban ointment, 2% in a polyethylene glycol base) and a chlorhexidine cream (1%) were used in a 1:1 ratio and mixed in situ, prior to application. It would however be more convenient to provide a single composition comprising mupirocin and chlorhexidine.

Preliminary studies had shown that merely admixing commercially available compositions of mupirocin and chlorhexidine gave compositions which were unstable. In addition, chlorhexidine is known to cause formulation problems because of its tendency to form insoluble salts. In principle, a salt could be formed with mupirocin which might cause problems. Surprisingly, it has now been found that pharmaceutical compositions with acceptable stability can be prepared, suggesting that excipients within the chlorhexidine composition originally used were incompatible with mupirocin.

Accordingly, the present invention provides for a pharmaceutical composition comprising:
from 0.01 to 10% by weight of mupirocin or a pharmaceutically acceptable salt or ester thereof; and
from 0.01 to 5% by weight of chlorhexidine or a pharmaceutically acceptable salt thereof;
in a vehicle comprising at least 50% by weight of a pharmaceutically acceptable poly (substituted or unsubstituted alkylene) glycol or a derivative thereof.

Such pharmaceutical compositions have an acceptable shelf life.

Suitable pharmaceutically acceptable salts are well known in the art and include alkali metal salts such as sodium and lithium and alkaline earth metal salts such as calcium, of which the calcium salt is preferred, in particular the crystalline dihydrate form thereof described in EP 0 167 856-A (Beecham Group), as well as other metal salts, for instance silver, aluminium, ammonium and substituted ammonium salts. The salts may be anhydrous or may be in the form of pharmaceutically acceptable solvates, for instance alcoholates and, especially, hydrates. Preferred salts include the calcium, silver and lithium salts, in particular the calcium salt. In the case of the calcium salt of mupirocin, the crystalline salt, preferably the crystalline hydrated calcium salt, more preferably the crystalline dihydrate salt, is used.

Suitable pharmaceutically acceptable esters are well known in the art and include lower alkyl esters, especially the methyl and ethyl esters.

Mupirocin is used in preference to a salt or ester thereof.

Suitably, mupirocin or a pharmaceutically acceptable salt or ester thereof is present in between 0.1 and 5%, preferably 0.5 and 5%, more preferably 1 and 3%, typically about 2%, by weight of the composition.

Suitable chlorhexidine salts are pharmaceutically acceptable and include the water soluble dihydrochloride, diacetate and digluconate salts.

Suitably, chlorhexidine digluconate is used. Suitably, chlorhexidine digluconate is incorporated into the formulation as the commercially available 20% aqueous solution.

Suitably, chlorhexidine or a pharmaceutically acceptable salt thereof is present in between 0.05 and 5, preferably 0.1 and 1.0%, more preferably 0.1 and 0.5% by weight of the composition (expressed as the weight of the free base). Typical compositions may comprise 0.2 or 0.5% by weight of the composition.

Suitable pharmaceutically acceptable poly (substituted or unsubstituted alkylene) glycols are well known in the art and include those having the following repeating unit:

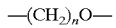

in which n is an integer, preferably 2 or 3, and
as well as those in which one or more methylene groups of each repeating unit is substituted.

Suitable substituents include alkoxy groups such as methoxy, as in polymethoxypropylene glycol. Such polymers are known by a variety of names, for instance when n=2, as polyethylene glycol, polyoxyethylene, polyoxyethylene glycol and macrogol and, when n=3, as polypropylene glycol, polyoxypropylene and polyoxypropylene glycol. All these are useful in the invention as are derivatives of these polymers.

Suitable derivatives include ethers and esters of the poly (substituted or unsubstituted alkylene) glycols, such as macrogol ethers and esters, for instance cetomacrogol; glycofurol; polyethoxylated sorbitol monoesters (for instance, Tweens, ICI); block copolymers including poly (substituted or unsubstituted alkylene) glycols such as block copolymers of polyethylene glycol and polypropylene glycol (poloxamers, for instance the 'Pluronics', BASF-Wyandotte); and cross-linked polyethylene glycols.

The poly (substituted or unsubstituted alkylene) glycols and derivatives thereof may be used singly, or various grades and types may be used in combination, to achieve the desired physical properties of the formulation.

Preferably the formulation comprises polyethylene glycol or a derivative thereof. Polyethylene glycols (PEG's) and derivatives thereof are commercially available in a variety of chain lengths and with a variety of consistencies. Suitable polyethylene glycols include PEG 200, PEG 300 and PEG 400 (liquids); PEG 1000 and PEG 1540 (semi-solids); and PEG 4000 and PEG 6000 (hard solids). PEG 4000 is the B.P. nomenclature for PEG with mean molecular weight of 3350. This material is also known as PEG 3350 in U.S.P. nomenclature.

Suitable polyethylene glycol derivatives include ethers and esters of the poly(substituted or unsubstituted alkylene glycols) such as macrogol ethers and esters, for instance cetomacrogol, glycofurol (tetrahydrofurfuryl alcohol polyethylene glycol ether) (liquid); Tween 60 (polyoxyethylene sorbitan monostearate) (semi-solid); and Tween 80 (polyoxyethylene sorbitan monooleate) (liquid).

These may be used singly or admixed in suitable proportions to achieve the desired consistency of formulation.

A preferred combination comprises PEG 4000 and PEG 400, suitably in a ratio of from 0.5:1 to 1:5, preferably from 1:1 to 1:2; more preferably about 1:1.5.

A preferred vehicle consists essentially of PEG 4000 and PEG 400, suitably in a ratio of from 0.5:1 to 1:5, preferably from 1:1 to 1:2; more preferably about 1:1.5, plus water derived from the chlorhexidine digluconate aqueous solution.

Typically, the vehicle comprises at least 60%, preferably at least 70%, more preferably at least 80%, most preferably at least 90% by weight of a pharmaceutically acceptable poly (substituted or unsubstituted alkylene) glycol or a derivative thereof.

Suitably, the compositions is adapted for topical administration.

Suitable such compositions include, for instance, ointments, creams or lotions, eye ointments and eye or ear drops and aerosols. In addition, compositions of the present invention may be used in impregnated dressings. Compositions of the present invention may also contain appropriate conventional additives such as preservatives, solvents to assist drug penetration and emollients in ointments and creams. The formulations may also contain conventional carriers such as cream or ointment bases and ethanol or oleyl alcohol for lotions.

Preferred compositions according to the present invention comprise:
from 0.5 to 5% by weight of mupirocin or a pharmacuetically acceptable salt or ester thereof; and
from 0.1 to 1% by weight of chlorhexidine or a pharmaceutically acceptable salt thereof;
in a vehicle comprising at least 50% by weight of polyethylene glycol or a mixture of polyethylene glycols and from 0 to 25% of a polyethylene glycol derivative or mixture of polyethylene glycol derivatives.

More preferred ointment compositions comprise:
from 1 to 3% by weight of mupirocin; and
from 0.1 to 1% by weight of chlorhexidine or a pharmaceutically acceptable salt thereof;
in a vehicle comprising a mixture of polyethylene glycol 4000 and polyethylene glycol 400 in a ratio 1:1 to 1:2.

Particularly preferred ointment compositions consist essentially of:
from 1 to 3% by weight of mupirocin; and
from 0.1 to 1% by weight of chlorhexidine or a pharmaceutically acceptable salt thereof;
in a vehicle comprising a mixture of polyethylene glycol 4000 and polyethylene glycol 400 in a ratio 1:1 to 1:2, present in at least 90% by weight of the vehicle.

Compositions of the present invention may be prepared by conventional pharmaceutical techniques. Thus, ointments and creams are conventionally prepared by mixing together the solid or semi-solid polyethylene glycols or derivatives thereof, and stirring in the therapeutic agents and any other ingredients. The product is then slowly cooled and filled into containers such as collapsible metal or plastic tubes.

Liquid preparations such as ear and eye drops, are produced by dissolving the therapeutic agents in the liquid polyethylene glycols or derivatives thereof and the other ingredients then added. The resulting solution or suspension is distributed into glass or plastic bottles or in single dose packs such as soft gelatin capsules which are then often heat sealed.

If necessary, the composition may be milled at any suitable stage of the process.

A suitable sterilisation step may be included in the above processes, if necessary. Alternatively, raw materials may be obtained in sterile conditions and the compositions then produced aspectically.

The combination of mupirocin and chlorhexidine provides an antibacterial regime which has a broader spectrum of activity than either agent alone. In particular, the combination has superior activity against Pseudomonas sp than either agent alone.

Preferably, compositions of the present invention are used for treating topical bacterial infections, in particular infected burns injuries. The method may also be used for the prophylatic treatment of burns injuries.

The invention will now be illustrated by the following Examples:

EXAMPLE

1. Ointment Comprising 2% Mupirocin and 0.5% Chlorhexidine

The composition per 100 g ointment is as follows:

| | |
|---|---|
| Mupirocin | 2.0 g |
| Chlorhexidine digluconate 20% aq soln | 4.44 ml |
| Polyethylene glycol 400 | 55.04 g |
| Polyethylene glycol 4000 | 37.23 g |

The composition was produced by melting the mixture of PEGs, stirring in the mupirocin and then stirring in the chlorhexidine digluconate solution.

The composition showed a satisfactory stability after 3 months at 37° C. and 75%RH and 9 months at 15–25° C. and ambient (55–80%) RH.

2. Ointment Comprising 2% Mupirocin and 0.2% Chlorhexidine

A further composition was prepared, using the proportions described above 1 except for chlorhexidine digluconate 20% aq soln (1.78 ml).

What is claimed is:

1. A pharmaceutical composition comprising:
   from 0.01 to 10% mupirocin or a pharmaceutically acceptable salt or ester thereof by weight of the composition; and
   from 0.01 to 5% chlorhexidine or a pharmaceutically acceptable salt thereof by weight of the composition
   in a vehicle comprising at least 50% by weight of a pharmaceutically acceptable poly (substituted or unsubstituted alkylene) glycol or a derivative thereof.

2. The composition as claimed in claim 1 comprising:
   from 1 to 3% mupirocin or a pharmaceutically acceptable salt or ester thereof by weight of the composition; and
   from 0.1 to 1% chlorhexidine or a pharmaceutically acceptable salt thereof by weight of the composition;

in a vehicle comprising a mixture of polyethylene glycol 400 and polyethylene glycol 4000.

3. The composition as claimed in claim 1 comprising:

from 1–3% mupirocin by weight of the composition; and from 0.1 to 1% chlorhexidine or a pharmaceutically acceptable salt thereof by weight of the composition;

in a vehicle comprising a mixture of polyethylene glycol 4000 and polyethylene glycol 400 in a ratio of about 1:1.5, present in at least 90% by weight of the vehicle.

4. The composition as claimed in claim 1 which comprises mupirocin, present in about 2% by weight of the composition.

5. The composition as claimed in claim 1 which comprises chlorhexidine digluconate.

6. The composition as claimed in claim 5, wherein the chlorhexidine digluconate is present in about 0.5% (expressed as the free base) by weight of the composition.

7. The composition as claimed in claim 6, wherein the chlorhexidine digluconate is present in about 0.2% (expressed as the free base) by weight of the composition.

8. A method of treating topical bacterial infections which comprises administering a pharmaceutical composition according to claim 1 to a patient in need thereof.

9. A method of treating infected burn injuries which comprises administering a pharmaceutical composition according to claim 1 to a patient in need thereof.

10. The composition as claimed in claim 1, wherein the chlorhexidine salt is a water soluble salt.

11. The composition as claimed in claim 5, wherein the chlorhexidine digluconate is incorporated into the formulation as an aqueous solution.

* * * * *